(12) United States Patent
Al-Ali et al.

(10) Patent No.: US 8,233,955 B2
(45) Date of Patent: Jul. 31, 2012

(54) OPTICAL SENSOR INCLUDING DISPOSABLE AND REUSABLE ELEMENTS

(75) Inventors: Ammar Al-Ali, Tustin, CA (US); Yassir Abdul-Hafiz, Irvine, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 1547 days.

(21) Appl. No.: 11/606,455

(22) Filed: Nov. 29, 2006

(65) Prior Publication Data

US 2007/0123763 A1 May 31, 2007

Related U.S. Application Data

(60) Provisional application No. 60/740,541, filed on Nov. 29, 2005.

(51) Int. Cl.
*A61B 5/1455* (2006.01)
(52) U.S. Cl. ........ 600/344; 600/310
(58) Field of Classification Search ......... 600/309–344
See application file for complete search history.

(56) References Cited

U.S. PATENT DOCUMENTS

| | | |
|---|---|---|
| 4,621,643 A | 11/1986 | New, Jr. et al. |
| 4,685,464 A | 8/1987 | Goldberger et al. |
| 4,700,708 A | 10/1987 | New, Jr. et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,090,410 A | 2/1992 | Saper et al. |
| 5,094,240 A | 3/1992 | Muz |
| 5,158,323 A | 10/1992 | Yamamoto et al. |
| 5,163,438 A | 11/1992 | Gordon et al. |
| 5,170,786 A | 12/1992 | Thomas et al. |
| 5,209,230 A | 5/1993 | Swedlow et al. |
| 5,337,744 A | 8/1994 | Branigan |
| D353,195 S | 12/1994 | Savage et al. |
| D353,196 S | 12/1994 | Savage et al. |
| 5,387,122 A | 2/1995 | Goldberger et al. |
| 5,431,170 A | 7/1995 | Mathews |
| D361,840 S | 8/1995 | Savage et al. |
| 5,437,275 A | 8/1995 | Amundsen et al. |
| D362,063 S | 9/1995 | Savage et al. |
| 5,452,717 A | 9/1995 | Branigan et al. |
| D363,120 S | 10/1995 | Savage et al. |

(Continued)

FOREIGN PATENT DOCUMENTS

AU 200010929 B2 5/2000

(Continued)

OTHER PUBLICATIONS

PCT International Search Report, App. No. PCT/US 2006/046176, App. Date: Nov. 29, 2006, 4 pages. European Examination Report re EPO Application No. 06 83 8888.3, dated Sep. 27, 2011.

*Primary Examiner* — Eric Winakur
*Assistant Examiner* — Marjan Fardanesh
(74) *Attorney, Agent, or Firm* — Knobbe Martens Olson & Bear LLP

(57) ABSTRACT

An embodiment of the present disclosure provides a noninvasive optical sensor or probe including disposable and reusable components. The assembly of the disposable and reusable components is straightforward, along with the disassembly thereof. During application to a measurement site, the assembled sensor is advantageously secured together while the componentry is advantageously properly positioned.

10 Claims, 14 Drawing Sheets

U.S. PATENT DOCUMENTS

| | | |
|---|---|---|
| 5,482,036 A | 1/1996 | Diab et al. |
| 5,490,505 A | 2/1996 | Diab et al. |
| 5,494,043 A | 2/1996 | O'Sullivan et al. |
| 5,507,286 A | 4/1996 | Solenberger |
| 5,533,511 A | 7/1996 | Kaspari et al. |
| 5,562,002 A | 10/1996 | Lalin |
| 5,590,649 A | 1/1997 | Caro et al. |
| 5,602,924 A | 2/1997 | Durand et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,664,270 A | 9/1997 | Bell et al. |
| 5,673,693 A | 10/1997 | Solenberger |
| 5,678,544 A | 10/1997 | DeLonzor et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,817,008 A | 10/1998 | Rafert et al. |
| 5,817,010 A | 10/1998 | Hibl |
| 5,823,950 A | 10/1998 | Diab et al. |
| 5,830,131 A | 11/1998 | Caro et al. |
| 5,833,618 A | 11/1998 | Caro et al. |
| RE36,000 E | 12/1998 | Swedlow et al. |
| 5,860,919 A | 1/1999 | Kiani-Azarbayjany et al. |
| 5,879,373 A | 3/1999 | Röper et al. |
| 5,890,929 A | 4/1999 | Mills et al. |
| 5,904,654 A | 5/1999 | Wohltmann et al. |
| 5,910,108 A | 6/1999 | Solenberger |
| 5,919,133 A | 7/1999 | Taylor et al. |
| 5,919,134 A | 7/1999 | Diab |
| 5,934,925 A | 8/1999 | Tobler et al. |
| 5,940,182 A | 8/1999 | Lepper, Jr. et al. |
| 5,991,648 A | 11/1999 | Levin |
| 5,995,855 A | 11/1999 | Kiani et al. |
| 5,997,343 A | 12/1999 | Mills et al. |
| 5,999,834 A | 12/1999 | Wang et al. |
| 6,002,952 A | 12/1999 | Diab et al. |
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,045,509 A | 4/2000 | Caro et al. |
| 6,061,584 A | 5/2000 | Lovejoy et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,308,089 B1 | 10/2001 | von der Ruhr et al. |
| 6,321,000 B1 | 11/2001 | King |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,381,489 B1 | 4/2002 | Ashibe |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,519,484 B1 | 2/2003 | Lovejoy et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |

| | | |
|---|---|---|
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 2001/0029325 A1 | 10/2001 | Parker |
| 2002/0045807 A1* | 4/2002 | Al-Ali et al. ............ 600/323 |
| 2003/0009092 A1 | 1/2003 | Parker |
| 2004/0147822 A1* | 7/2004 | Al-Ali et al. ............ 600/323 |

FOREIGN PATENT DOCUMENTS

| | | |
|---|---|---|
| CA | 2 346 639 | 4/2000 |
| CA | 2 366 493 A1 | 11/2002 |
| EP | 1 222 894 A2 | 7/2002 |
| EP | 1 222 894 A3 | 7/2002 |
| WO | WO 00/21433 | 4/2000 |
| WO | WO 01/03574 | 1/2001 |
| WO | WO 01/03574 A1 | 1/2001 |
| WO | WO 02/089664 | 11/2002 |

\* cited by examiner

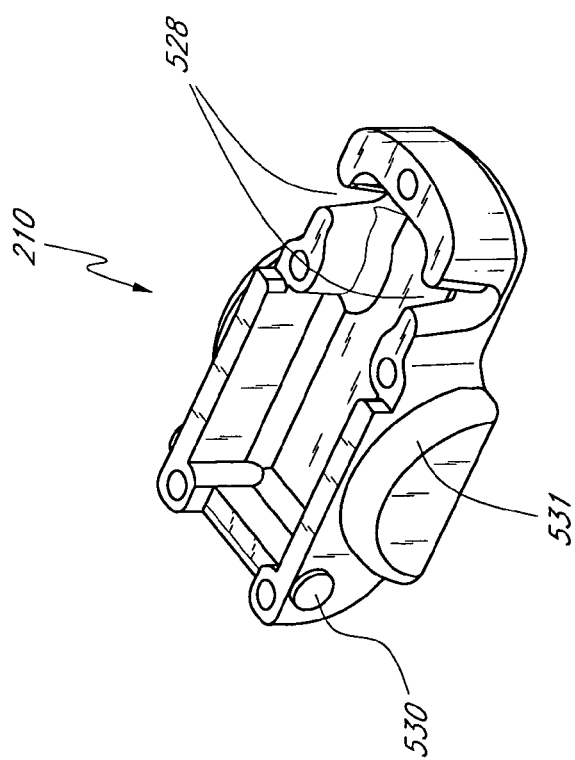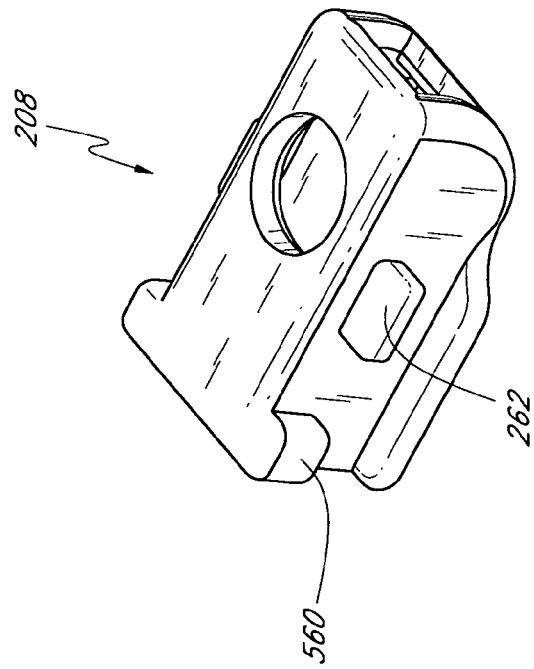

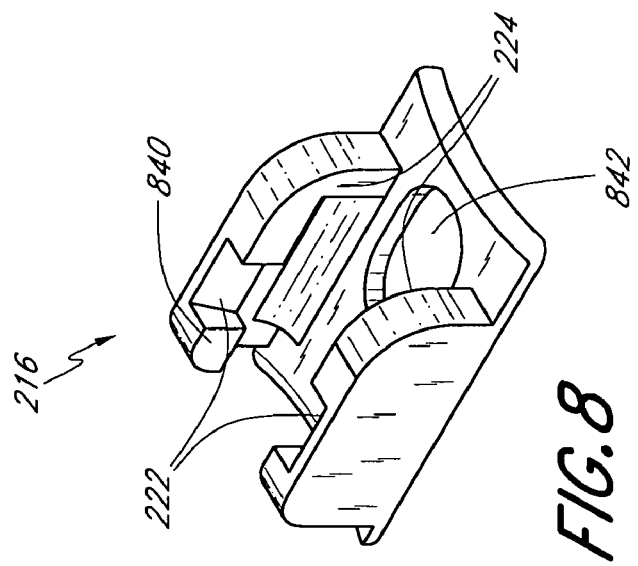
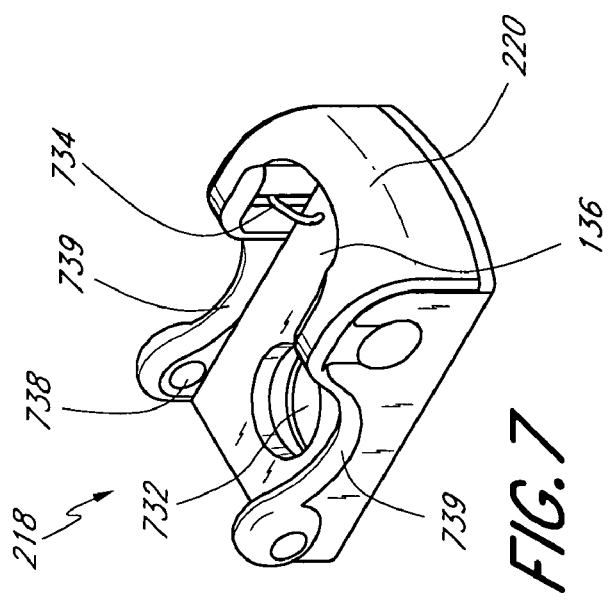
FIG. 8
FIG. 7

OPTICAL SENSOR INCLUDING DISPOSABLE AND REUSABLE ELEMENTS

PRIORITY CLAIM

This application claims priority benefit under 35 U.S.C. §119(e) from U.S. Provisional Application No. 60/740,541, filed Nov. 29, 2005, entitled "Optical Sensor Including Disposable and Reusable Elements." The present application incorporates the foregoing disclosure herein by reference.

REFERENCE TO RELATED APPLICATIONS

This application also relates to U.S. Pat. No. 6,920,345, filed on Jan. 24, 2003 and issued on Jul. 19, 2005, entitled "Optical Sensor Including Disposable And Reusable Elements." The present application also incorporates the foregoing disclosure herein by reference.

BACKGROUND OF THE DISCLOSURE

1. Field of the Disclosure

The present disclosure relates to noninvasive optical sensors capable of detecting light attenuated by body tissue. More specifically, the disclosure relates to the combination of reusable and disposable components of such sensors.

2. Description of the Related Art

Early detection of low blood oxygen is important in a wide range of applications, including patient monitoring, the fitness industry, home care and the like. Noninvasive oximetry was developed to study and to measure, among other things, the oxygen status of blood. Pulse oximetry—a noninvasive, widely accepted form of oximetry—relies on a sensor attached externally to a patient to output signals indicative of various physiological parameters, such as a patient's blood oxygen saturation.

A pulse oximeter sensor generally includes one or more energy emission devices, such as specific wavelength emitting LEDs, and one or more energy detection devices. The sensor is generally attached to a measurement site such as a patient's finger, ear, ankle, or the like, using an attachment mechanism such as a disposable tape, reusable housing, a plastic or hook-and-loop fastening strap, or the like. The attachment mechanism positions the emitters and detector proximal to the measurement site such that the emitters project energy into the blood vessels and capillaries of the measurement site, which in turn attenuate the energy. The detector then detects that attenuated energy. The detector communicates at least one signal indicative of the detected attenuated energy to a signal processing device such as an oximeter. The oximeter generally calculates, among other things, one or more physiological parameters of the measurement site.

Noninvasive oximetry sensors can be disposable, reusable, or some combination thereof. Reusable sensors offer advantages of superior cost savings. However, reusable sensors are often available in a limited number of sizes even though patient measurement sites, such as fingers or toes, can have a much larger size distribution. Therefore, sometimes reusable sensors do not readily conform to each patient's measurement site. Disposable sensors on the other hand offer superior conformance to the measurement area. However, disposable sensors are generally more costly due to limited use of the relatively expensive sensor components which could otherwise last for repeated uses.

Faced with the drawbacks of reusable and disposable sensors, manufacturers began designing a number of middle-ground sensors. For example, some manufacturers offer a reusable detector portion that couples to a disposable emitter portion. After a single use, the disposable emitter portion is detached from the reusable detector portion and discarded. While this design reuses some of the expensive electronic components, obviously others are still discarded.

Another example of a middle-ground sensor includes a reusable "Y" type sensor, where a reusable emitter portion connects to one branch of the "Y" while a reusable detector portion connects to the other branch. A disposable tape positions the two branches on a measurement site. In this design, the electronics are reusable; however, the multiple wires tend to be somewhat difficult to properly attach, especially with a moving patient.

Other examples of middle-ground sensors include a disposable tape sandwich where a reusable flexible circuit housing an emitter portion and a detector portion, are "sandwiched" between adhesive layers. Separation of such disposable tape sandwiches can be cumbersome. In yet another example of a middle-ground sensor, the Assignee of the present application disclosed a reusable flexible circuit that is snapped into a disposable tape. In an embodiment of that disclosure, small pegs on the flexible circuit snap into mechanically mating elements on the disposable tape. Grooves allow some longitudinal travel between the reusable portion and the disposable portion, thereby allowing for some self adjustment between components to account for differences in radial attachment requirements.

SUMMARY OF THE DISCLOSURE

However, even with the advances discussed in the foregoing, there continues to be a need for a commercially viable, straightforward, middle-ground solution that offers reusability of expensive electronic components while maintaining some of the advantages of disposable attachment.

Accordingly, one aspect of an embodiment of the present disclosure is to provide a sensor having reusable and disposable components. In an embodiment, the sensor advantageously includes a disposable component structured to provide a locking feature capable of reducing a chance that the disposable and reusable components can separate when attached or otherwise in close proximity to the body. In an embodiment, a locking mechanism takes advantage of longitudinal displacement and engages when the reusable and disposable portions of the sensor are curved around the measurement site (such as a finger). Separation of the reusable portion from the disposable portion is then advantageously complicated until the sensor is removed from the patient and the displacement is reversed.

A further aspect of an embodiment of this disclosure is that the tip of the reusable sensor component slides angularly into the front housing component on the disposable portion before sitting flat in a slot or guide. The slot or guide includes a rubber stop that in an embodiment advantageously provides a fluid-tight or at least fluid resistant contact.

In a further embodiment, a memory device or information element is provided as part of the disposable housing. An electrical contact is made between the memory device and the reusable components to, for example, ensure quality control in the disposable housing, provide information to the patient monitor about the type of sensor, type of patient, type of attachment mechanism or attachment position, information about operating characteristics of the sensor, product manufacture or sale history, distributor history, amount of use, combinations of the same or the like.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The following drawings and the associated descriptions are provided to illustrate embodiments of the present disclosure and do not limit the scope of the claims.

FIG. 5A-5B illustrate top and bottom perspective views of a detector casing or housing of the reusable component, according to an embodiment of the disclosure.

FIG. 6A-6B illustrate top and bottom perspective views of an emitter casing or housing of the reusable component, according to an embodiment of the disclosure.

FIG. 7 illustrates a perspective view of a front holding clip of the disposable component, the clip being capable of mechanically mating with the detector casing of FIG. 5, according to an embodiment of the disclosure.

FIG. 8 illustrates a perspective view of the assembly/disassembly clip of the disposable component, the clip being capable of mechanically mating with the emitter casing of FIG. 6, according to an embodiment of the disclosure.

DETAILED DESCRIPTION

Figure 1:
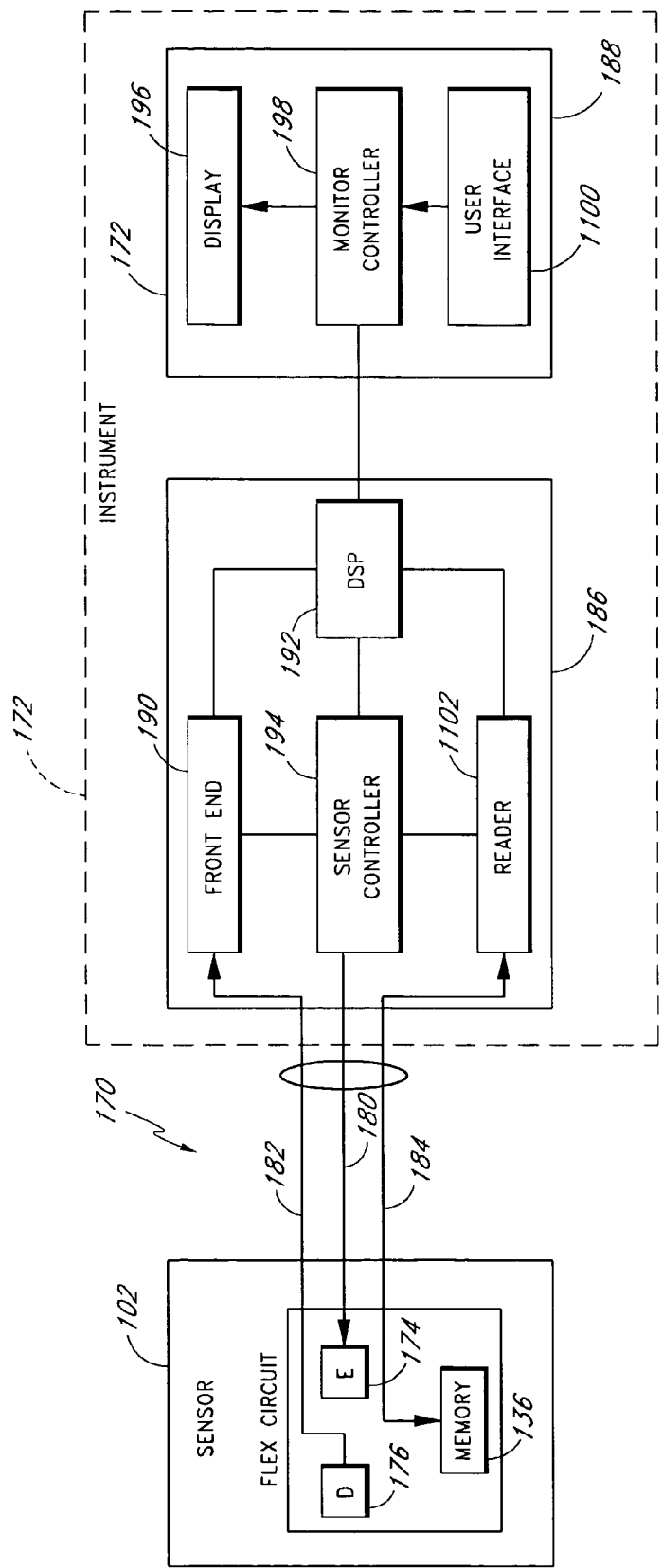
FIG. 1 illustrates an exemplary block diagram of an oximeter system including a sensor and a monitoring instrument, according to embodiments of the disclosure.

An embodiment of the present disclosure is a sensor with a reusable component and a disposable component. The reusable component generally includes reusable expensive electronic components of a sensor, including, for example, the emitters and detector. In an embodiment, the emitters and the detector are located in respective casings connected by a short flexible circuit. In an embodiment, a disposable component includes mechanically matable portions adapted to mechanically mate with the casings of the reusable component. In an embodiment, the casings of the reusable component mate with the disposable component in a manner that provides an assembly/disassembly state, and an attached state. During the assembly/disassembly state, a caregiver can readily and straightforwardly assemble the sensor by aligning the casings on the reusable component and the mechanical housings of the disposable component and snapping them together. In an embodiment, the alignment is generally vertical in nature and the snapping occurs by lightly pressing on the components while on a flat surface or supported from underneath by, for example, the hand of the assembler. Each detector housing generally vertically accepts the casings; however, one of the casings, such as, for example, the forward housing or clip accepts the casing in such a way as to keep the forward casing generally immobile.

Disassembly is equally as straightforward, as the caregiver may advantageously lift on the reusable component wire, and the rearward casing extracts from the mechanically mated housing of the disposable element. Continual lifting then similarly extracts the forward casing from the mechanically mated housing of the disposable element. In an embodiment, the flexible circuit between the forward and rearward casing may be reinforced in order to withstand multiple disassembly stresses or forces occurring from the lifting of the reusable wire. In an embodiment, pressing the disposable portion onto a flat surface while lifting the reusable portion aids in the disassembly process.

The disposable portion includes structures designed to attach the sensor to a measurement site. In an embodiment, the disposable portion comprises a flexible tape having an adhesive side capable of removably adhering to the measurement site. In an embodiment where the disposable portion wraps around a measurement site, the act of bending the flexible circuit advantageously causes the assembly/disassembly clip to recess into the mechanically mated portion of the disposable housing, thereby reducing the likelihood of disassembly during application to a measurement site. In an embodiment, the sensor components are locked together through the longitudinal displacement of the clip with respect to the disposable housing. In such an embodiment, a stop diminishes the capacity of the clip to move vertically, thereby locking it into place. In this embodiment, removing the adhesive from the measurement site and straightening the sensor components unlocks the reusable and disposable components.

In an embodiment, assembly also necessarily electrically connects electronic components of the disposable portion with those of the reusable portion. In an embodiment, then disposable portion includes an information element or memory device, such as, for example, a resistor, a single wire addressable memory device, such as those EPROMs or EEPROMs commercially available from Dallas Semiconductor, other memory or processing devices, combinations of the same, or the like. The information element may include data accessibly by an attached patient monitor to accomplish quality control, monitor configuration, sensor use monitoring, combinations of the same, or the like.

Still other advantages of embodiments of the present disclosure include proportionally positioning of the mechanically mating housings to provide for optical alignment between the emitters and detector. Moreover, in embodiments including the disposable tape, the tape may advantageously be scored to assist the caregiver in proper alignment with the body tissue at the measurement site.

To facilitate a complete understanding of the disclosure, the remainder of the detailed description describes the disclosure with reference to the drawings. Corresponding parts refer to corresponding elements and the leading digit indicates the figure in which that element first appears.

General Design

FIG. 1 presents an exemplary block diagram of the components generally found in an oximeter sensor, according to an embodiment of the invention. For example, FIG. 1 shows as oximeter system including sensor 102, cable 170, and monitor 172. The sensor 102 includes one or more emitters 174 for irradiating body tissue with light, and one or more detectors 176 capable of detecting the light after attenuation by the tissue. The sensor 102 also includes an information element 136 such as an EPROM. The sensor 102 also includes a plurality of conductors communicating signals; including emitter drive signal conductors 180, detector composite signal conductors 182, and EPROM conductors 184. According to an embodiment, the sensor conductors 180, 182, 184 communicate their signals to and from the monitor 172 through cable 170.

Although disclosed with reference to the cable 170, a skilled artisan will recognize from the disclosure herein that the communication to and from the sensor 102 may advantageously include a wide variety of cables, cable designs, public or private communication networks or computing systems, wired or wireless communications, combinations of the same, or the like.

The information element 136 may comprise an EPROM, an EEPROM, combinations of the same, or the like. In general, the information element 136 may include a read-only device or a read and write device. The information element may advantageously also comprise a resistor, an active network, or any combination of the foregoing. The remainder of the present disclosure will refer to such possibilities as simply an information element for ease of disclosure.

The information element 136 may advantageously store some or all of a wide variety of data and information, including, for example, information on the type or operation of the sensor 102, type of patient or body tissue, buyer or manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, or monitor or algorithm upgrade instructions or data. The information element 136 may advantageously configure or activate the monitor, monitor algorithms, monitor functionality, or the like based on some or all of the foregoing information. For example, without authorized data accessibly on the information element 136, quality control functions may inhibit functionality of the monitor. Likewise, particular data may activate certain functions while keeping others inactive. For example, the data may indicate a number of emitter wavelengths available, which in turn may dictate the number and/or type of physiological parameters that can be monitored or calculated.

FIG. 1 also shows the monitor 172 comprising one or more processing boards 186 communicating with one or more host instruments 188. According to an embodiment, the board 186 comprises processing circuitry arranged on one or more printed circuit boards capable of being installed in specialized monitoring equipment or distributed as an OEM component for a wide variety of patient monitoring equipment. As shown in FIG. 1, the board 186 includes a front end signal conditioner 190, a sensor controller 194, a digital signal processor or microcontroller 192, and a memory reader 1102. In an embodiment, the processor 192 instructs the sensor controller 194 to output one or more drive signals capable of causing the emitters 174 to activate. The front end 190 receives detector output indicating detection of light from the emitters 174 attenuated by body tissue of the measurement site. The front end 190 conditions the signal and outputs the signal and/or signal data to the processor 192. The processor 192 executes calculations adapted to determine values and/or indications or physiological parameters, trends of the parameters, alarms based on the parameters or the trends or combinations of trends and/or parameters, or the like. In addition, the reader 1102 is capable of retrieving information stored on information element 136. The reader 1102 or the processor 192 may advantageously decrypt such information to the extent desired.

In an embodiment, the host instrument 188, communicates with the processor 192 to receive signals indicative of the physiological parameter information calculated by the processor 192. The host instrument preferably includes one or more display devices 196 capable of providing indicia representative of the calculated physiological parameters of the tissue at the measurement site. Such display devices 196 may be controlled by a monitor controller 198 that accepts signals from processor 192. In an embodiment, monitor controller 198 may also accept signals from user interface 1100. Such signals may be indicative of various display options for configuring the output to display 196. In an embodiment, the host instrument 188 may advantageously be capable of displaying one or more of a pulse rate, plethysmograph data, perfusion quality, signal or measurement quality, values of blood constituents in body tissue, including for example, SpCO, functional or fractional $SpO_2$, or the like. In other embodiments, the host instrument 188 is capable of displaying values for one or more of SpMet, $HbO_2$, Hb, HbCO, HbMet, Hct, blood glucose, bilirubin, or the like. In still additional embodiments, the host instrument 188 is capable of displaying trending data for one or more of the foregoing measured or determined data. Moreover an artisan will realize from the disclosure herein many display options for the data are available.

In an embodiment, the host instrument 188 includes audio or visual alarms that alert caregivers that one or more physiological parameters are falling below predetermined safe thresholds, and may include indications of the confidence a caregiver should have in the displayed data. In further embodiment, the host instrument 188 may advantageously include circuitry capable of determining the expiration or overuse of components of the sensor 102, including for example, reusable elements, disposable elements, or combinations of the same.

Although disclosed with reference to particular embodiment, an artisan will recognize from the disclosure herein many variations of the instrument 172. For example, in a broad sense, the instrument 172 accepts data from the sensor 102, determines values for one or more parameters, trends, alarms or the like, and outputs them to an interface such as a display.

Sensor Configuration

Figure 2:
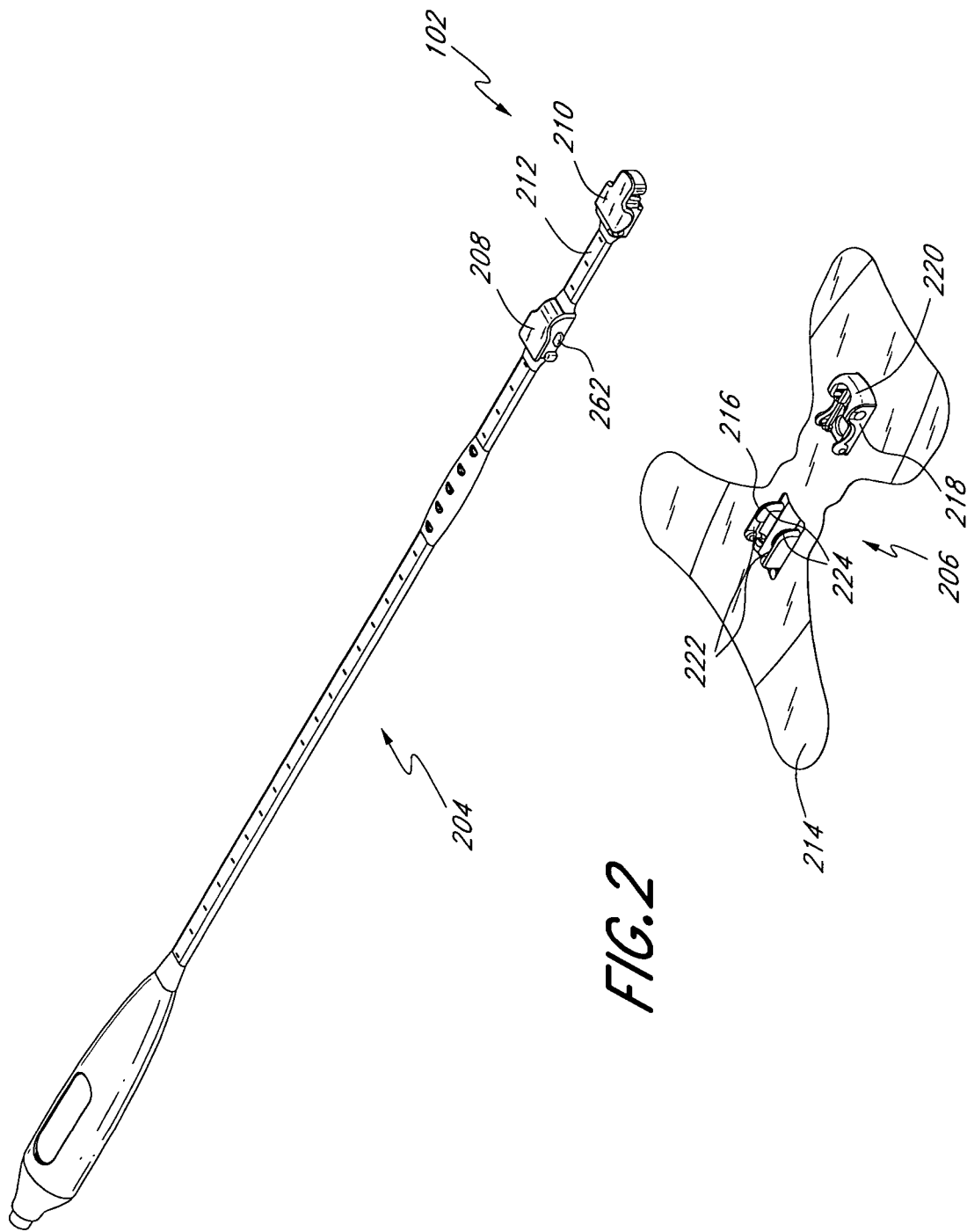
FIG. 2 illustrates a perspective view of the sensor of FIG. 1, where reusable and disposable components of the sensor are separated according to an embodiment of the disclosure.

FIG. 2 illustrates an embodiment of sensor 102, having reusable component 204 and disposable component 206. The components are shown detached. FIG. 3 shows a very similar perspective drawing, but with reusable component 204 and disposable component 206 in their attached, in their assembled state. Returning to FIG. 2, the reusable component 204 comprises an emitter casing 208, a detector casing 210, and a flexible circuit 212. The emitter casing 208 comprises one or more emission devices operable to emit light at multiple wavelengths, such as red and infrared. Detector casing 210 houses one or more detectors, such as a photodiode detector. In an embodiment, a flexible circuit connects the emitter casing 208 and detector casing 210. In a preferred embodiment, the flexible circuit is housed in a protective cover and extends beyond the emitter casing 208. An artisan will understand from the disclosure herein that the emitter and detector electrical components may advantageously be housed in the casings disclosed or simply reversed from the foregoing disclosure. In an embodiment, the flexible circuit 212 and/or cabling extends significantly beyond the casings to advantageously remove any cable attachment mechanisms from the proximity of the tissue site.

FIG. 2 also shows the disposable component 206 including a base 214, an assembly/disassembly clip 216 and a front holding clip 218, the clips each adapted to accept the emitter casing 208 and detector casing 210, respectively. In the preferred embodiment, front holding clip 218 includes a front stop 220. Front stop 220 is advantageous for a number of reasons. It helps reduce the likelihood that the reusable component 102, and in particular detector casing 210, will slide forward in the front holding clip 218 during assembly or use. In addition, in an embodiment where the stop 220 comprises rubber or other liquid resistant material, the stop 220 provides a liquid resistant connection between the detector casing 210 and front holding clip 218, reducing the likelihood of sensor contamination and electrical shorts. Rubber or a similar material may be used in an embodiment to compose such a front stop 220.

Figure 3A:
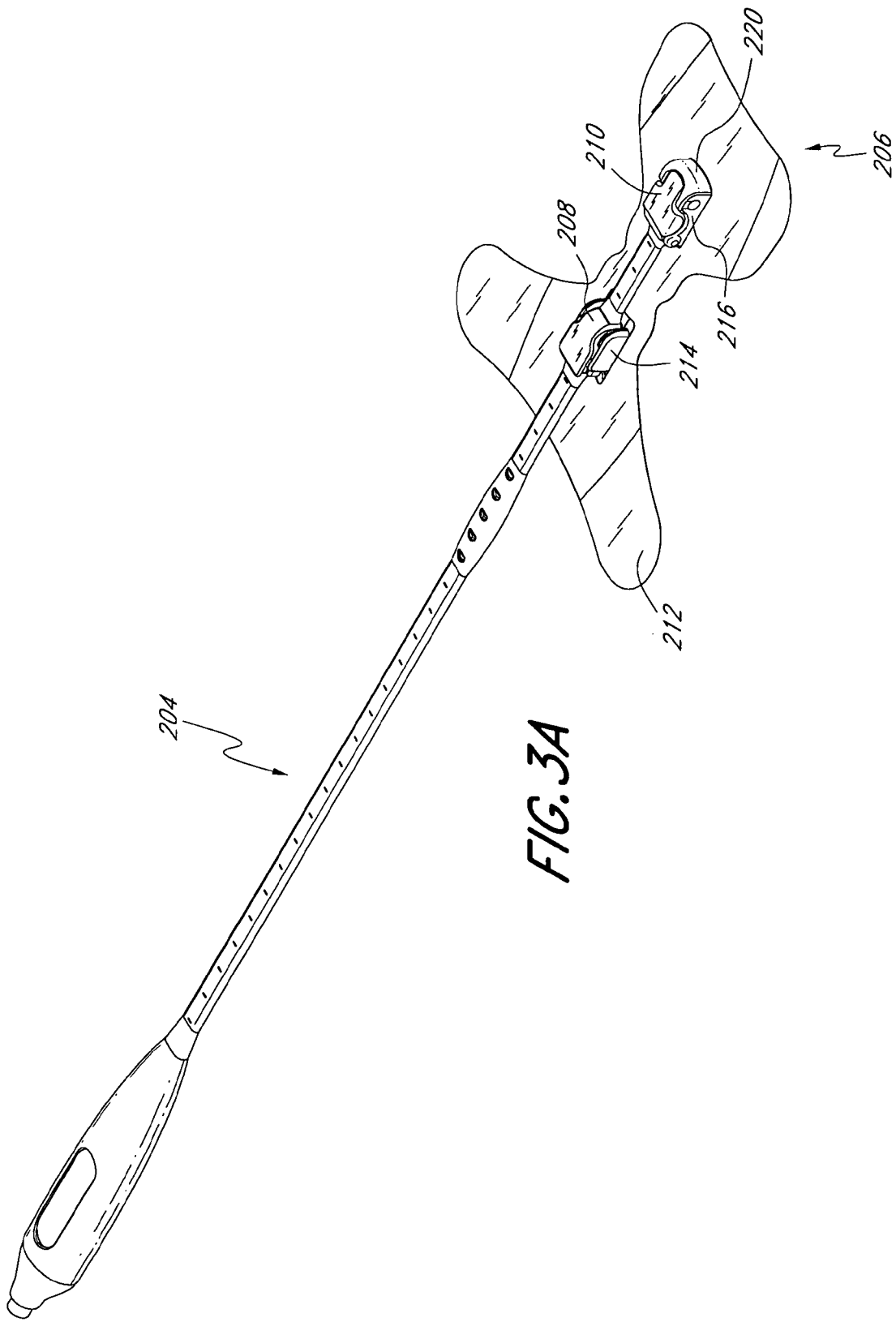
FIGS. 3A-3B illustrate perspective views of the sensor of FIG. 2, where the components are connected in an assembly/disassembly position, according to an embodiment of the disclosure.

FIG. 3A shows detector casing 210 clipped or snapped into front holding clip 218 with a tip of the casing slid below a portion of the front stop 220. This allows the front stop 220 to reduce not only horizontal movement of the detector casing 210, but also helps reduce vertical release of the detector casing unless pulled from, for example, the cable. FIG. 3 also shows the front stop 220 with a generally rounded shape providing a relatively soft material with few, if any, sharp edges. Such an embodiment advantageously reduces damage to a patient or the sensor if the patient tries to scratch body tissue using the edges of the assembled sensor, or if the sensor is dropped, banged against something while worn, or the like. This is particularly useful when used with burn victims or other patients whose skin may damage easily.

Figure 3B:
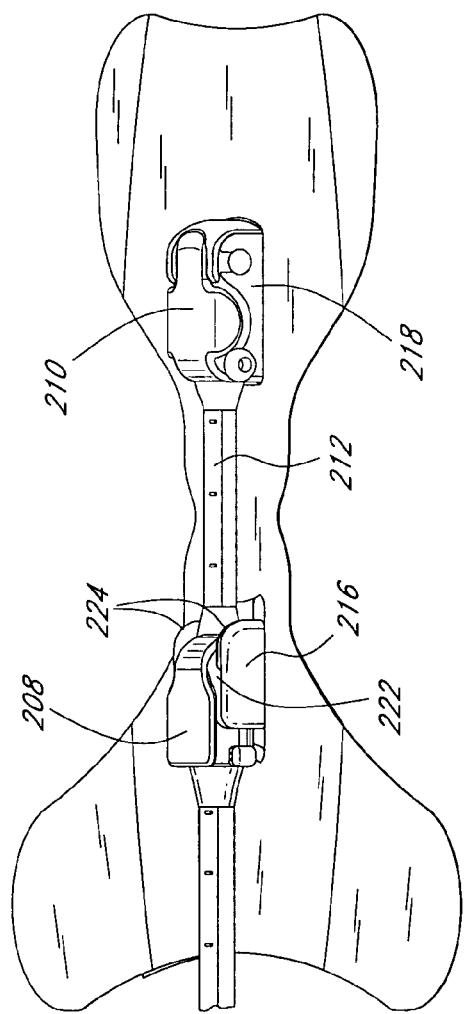

FIG. 3B highlights the ease of assembly. The disposable portion 206 is set on a surface or held in the one hand. The caregiver then aligns a front tip of casing 210 and guides it into front holding clip 218. This is more a vertical alignment with the front tip snapping below stop 220. The casing 210 including rounded wings 531 (FIG. 5) that mechanically associate with rounded side walls 739 (FIG. 7). These mechanical structures allow the tip of casing 210 to slide below stop 220, and snap down into place. Once casing 210 is in place, casing 208 aligns vertically and simply slides down, with tabs 262 (FIG. 6) located sliding into slots 222 (FIG. 8) on either side of assembly/disassembly clip 216. In an embodiment, the flexible circuit portion 212 between the casings 208 and 210 may bulge slightly.

Figure 4:
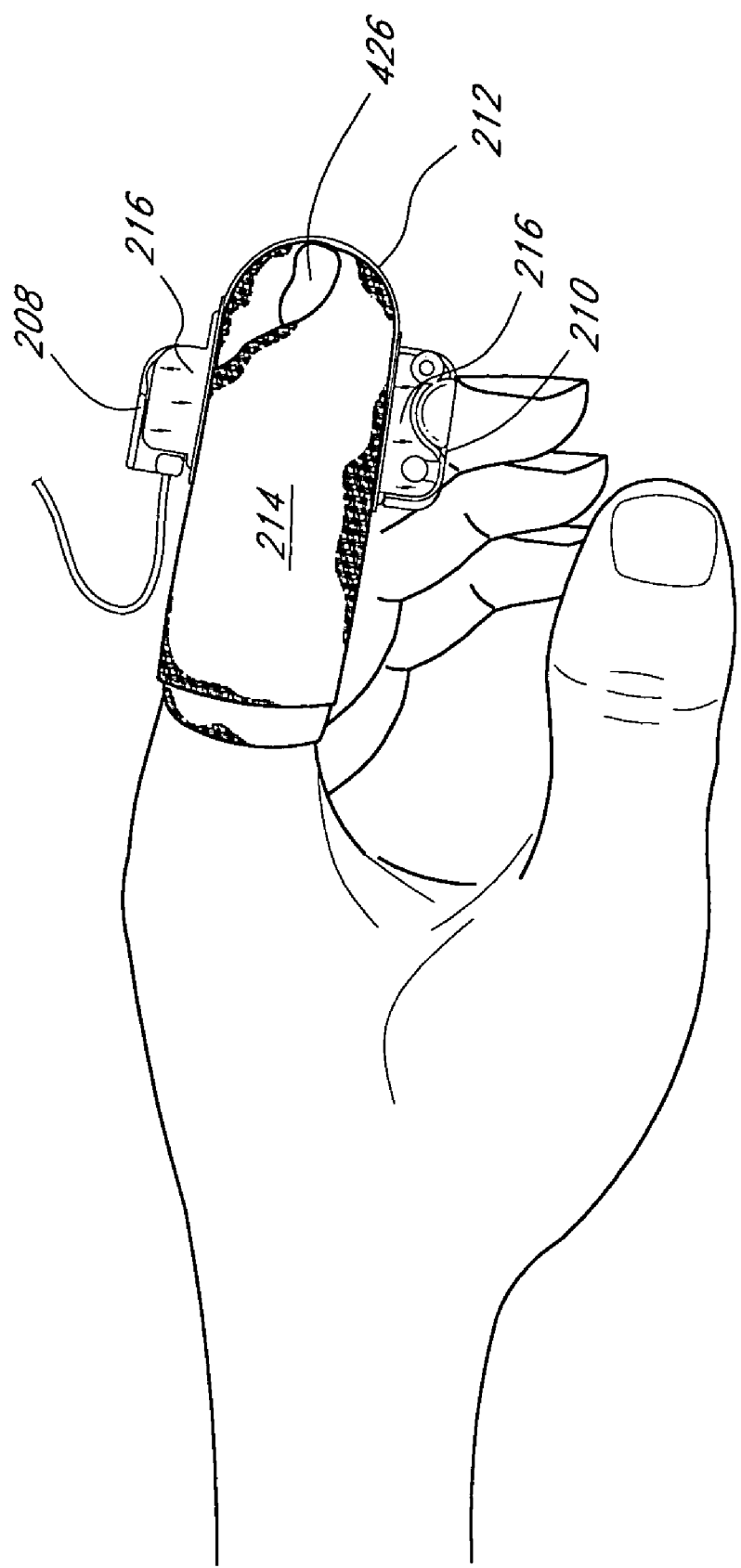
FIG. 4 illustrates a perspective side view of the sensor of FIG. 2, where the components are in an attached position, according to an embodiment of the disclosure.

FIG. 3B shows the emitter casing 208 after it has been slid onto assembly/disassembly clip 216. With the reusable sensor component 204 and the disposable sensor component 206 in a generally flat position, the emitter casing 208 remains vertically mobile in slots 222 of assembly/disassembly clip 216. When the sensor 102 is wrapped around a measurement site 426, such as a finger, as shown in FIG. 4, emitter casing 208 slides forward in assembly/disassembly clip 216 due to the tension from flexible circuit 212 and detector casing 210 being substantially immobile in front holding clip 218. Tabs 262 (FIG. 6) slide away from slots 222 (FIG. 8) and under holding elements 224 (FIG. 8). Holding elements 224 prevent emitter casing 208 from moving vertically or further forward by restricting tabs 262. As stated before, the tension from flexible circuit 212 when it is wrapped around a measurement site 426 prevents the emitter casing 208 from moving horizontally backwards. The immobility of casing 210, combined with the tabs 262 sliding out of alignment with slots 222, effectively secure the reusable sensor component 204 with respect to disposable component 206, with the emitters appropriately position with respect to the detector. Thus, realignment through release of tension, i.e., removing the sensor from an attachment site and straightening it out, ensure straightforward disassembly of the sensor components. Although shown using tabs 262 and slots 222, a skilled artisan will recognize from the disclosure herein a wide variety of mechanical mechanisms that ensure reliable attachability when the sensor is applied to the tissue site and straightforward assembly/disassembly when the sensor is removed. For example, one or more detents that snap closed beyond a catch and are released through pinching could be used to secure the reusable portion 204 to the disposable portion 206.

As alluded to previously, FIG. 4 depicts sensor 102 as would be seen when in use on a measurement site 426. In this case, the measurement site is a finger, but other sites such as a toe, ear, wrist or ankle may also work. Disposable component 206 and reusable component 204 are attached, and reusable component 204 is in the assembled and attached position. Longitudinal tension on the flexible circuit 212 from the differing radius between the tape and the circuit has pulled the emitter casing 208 forward, placing tabs 262 under holding elements 224. FIG. 4 shows that, in an embodiment, emitter casing 208 is rearward with respect to assembly/disassembly clip 216 when in the unattached position (FIG. 3B), but the front of emitter casing 208 is forward and in an embodiment, generally flush with assembly/disassembly clip 216 when in the attached position (FIG. 4).

Figure 5A:
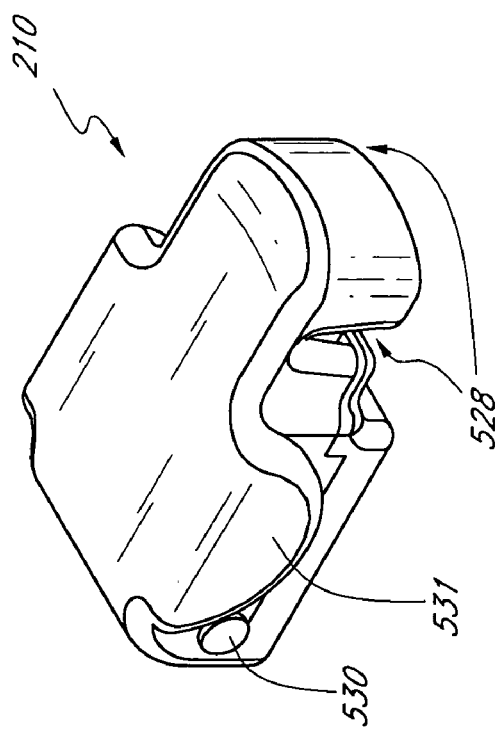

FIGS. 5A-5B show close up top and bottom perspective views of an embodiment of the detector casing 210. Electrical contact acceptors 528 are shown as insets on the sides of detector casing 210. In an embodiment, electrical contact acceptors 528 are located on either side of the detector casing 210 and include conductive material that would be connected to a wire in flexible circuit 212. Buttons 530 found on either side of the detector casing 210 are, in the preferred embodiment, generally hemispherical protrusions adapted to sit in depressions 738 found on front holding clip 218 (see FIG. 7).

FIG. 7 shows a close up perspective view of an embodiment of the front holding clip 218, again to show detail less easily seen in smaller figures. While most of the front sensor clip 218 may be made of plastic or some other rigid material, the preferred embodiment has front stop 220 made of rubber as has been discussed. Opening 732 is also shown here and may be a hole through front holding clip 218 or may just be of a generally transparent material that will allow light from the LEDs to enter the tissue at the measurement site and allow light energy to be read by the photodiode. Having window 732 be transparent material will allow the sensor to obtain readings while keeping the LEDs and photodiode from becoming contaminated. Other optical filters or the like could also be housed in window 732.

Located inside front stop 220 are conducting prongs 734. Conducting prongs 734 are adapted to fit into electrical contact acceptors 528. In an embodiment, the conducting prongs 734 close the circuit with the information element 136. When the detector casing 210 clips into front holding clip 218, the conducting prongs 734 slide into electrical contact with acceptors 528. The completed circuit allows the sensor 102, and in turn an oximeter, to communicate with information element 136. Depressions 738 are located on the interior of front holding clip 218. They are preferably generally hemispherical depressions similar in size to buttons 530, so as to accept buttons 530, and hold detector casing 210 in a substantially immobile position relative to front holding clip 218. Thus, a straightforward snap-in snap-out friction fit is accomplished using buttons 520 and depressions 738.

Figure 6A:
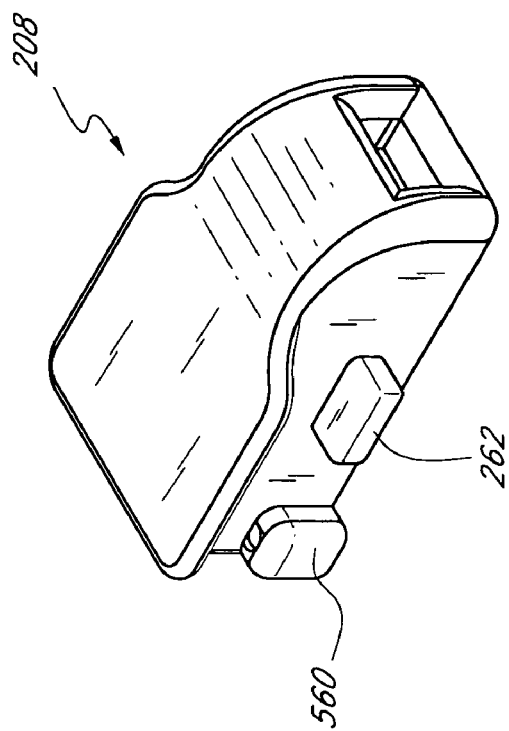

FIGS. 6A-6B show close up top and bottom perspective views of emitter casing 208. Rear pegs 660 are located on either side of emitter casing 208. When tabs 262 slide down slots 222 of assembly/disassembly clip 216, rear alignment pegs 660 slide down behind assembly/disassembly clip 216. Rear pegs 660 provide further restriction from forward movement, and structural support integrity, once emitter casing 208 has slid into a locking position by hitting rear stops 840 in assembly/disassembly clip 216 (See FIG. 8).

FIG. 8 illustrates a close-up perspective view of a assembly/disassembly clip 216 according to the preferred embodiment. As discussed emitter casing 208, slides down into assembly/disassembly clip 216 with tabs 262 passing through slots 222 and rear pegs 660 passing behind assembly/disassembly clip 216. As emitter casing 208 slides forward due to pull from application to a user, tabs 262 generally restrict over-forward movement or any vertical movement by abutting holding elements 224. Rear pegs 660 also generally abut rear stops 840. Assembly/disassembly clip 216 also has a window 842 that is substantially similar to window 732 on the front holding clip 218.

Figure 9:
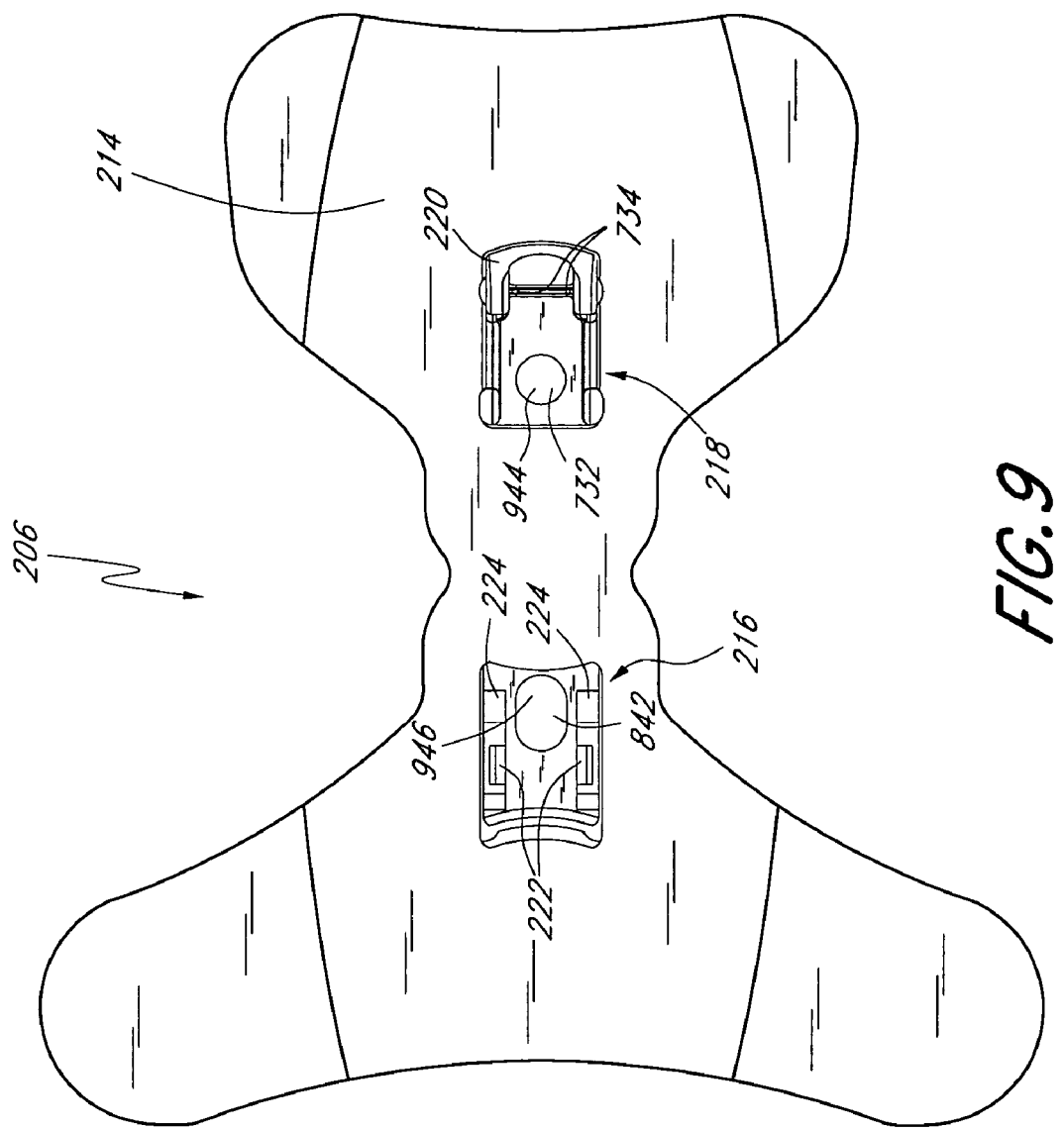
FIG. 9 illustrates a top planar view of the disposable component including the front holding clip and the assembly/disassembly clip of FIGS. 7-8, according to an embodiment of the disclosure.

FIG. 9 shows a top down view of the disposable sensor element. As shown in FIG. 9, the assembly/disassembly clip 216 and the slots 222 that allow vertical entry of the tabs 262 and the emitter casing 208. Moreover, FIG. 9 shows windows 842 and 732 in assembly/disassembly clip 216 and front holding clip 218, respectively. FIG. 9 also shows windows 944 and 946. Windows 944, 946 are included in the base 214. Like the openings 732, 842, windows 944, 946 may either be holes through base 214, or they may be of a material allowing free light transmission. Windows 944, 946 generally align with openings 732 and 842 to provide optical access to the measurement site for the emitters and detectors of the sensor. FIG. 9 also shows the contact prongs 734 on the insides of front holding clip 218. The contact prongs 734 connect the reusable sensor component 204 to information element 136, which may be variously utilized such as for storing information relating to the sensor's manufacturer or the like.

Manufacture

Figure 10:
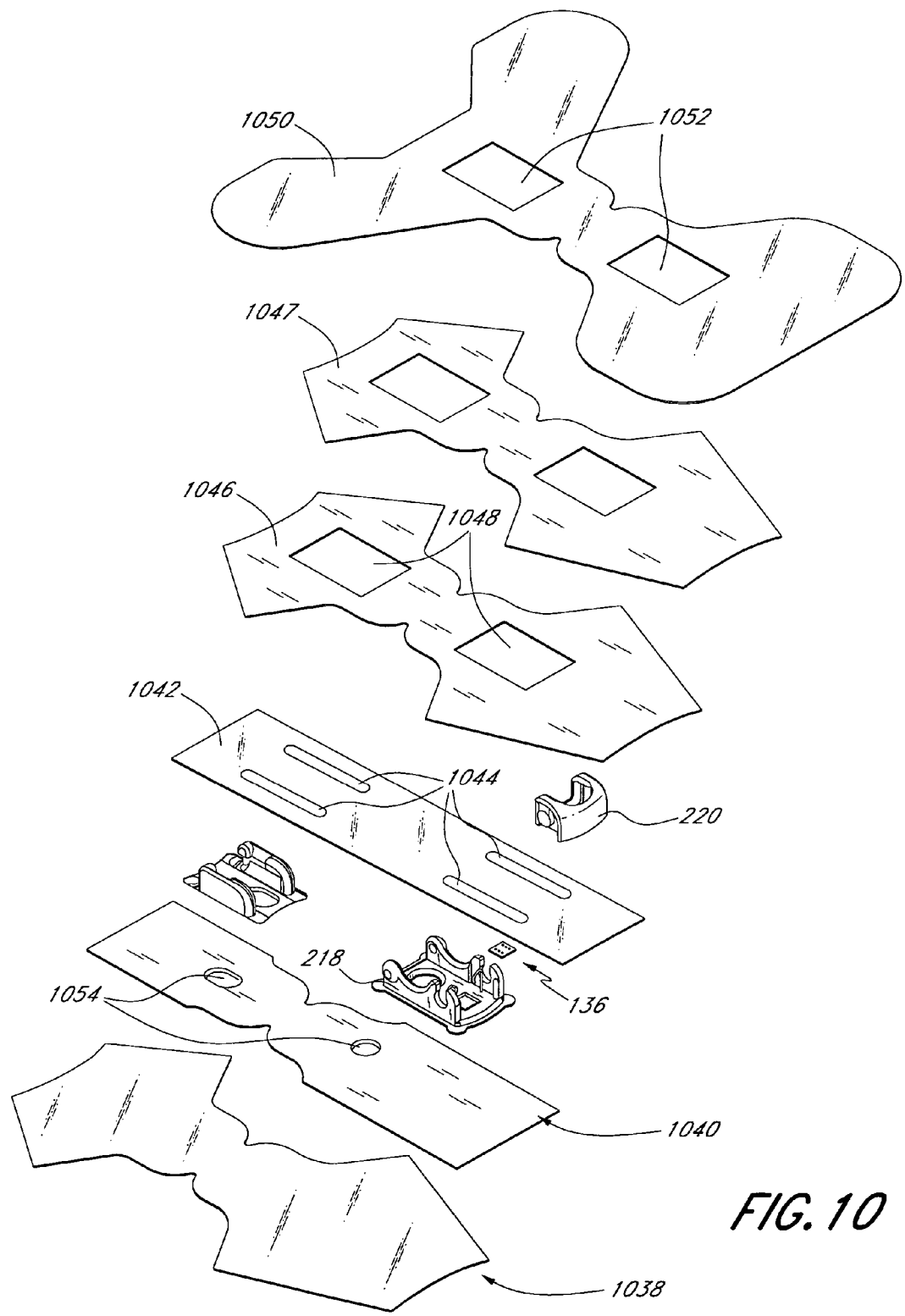
FIG. 10 illustrates an exploded view of the disposable component, according to an embodiment of the disclosure.
Figure 10B:
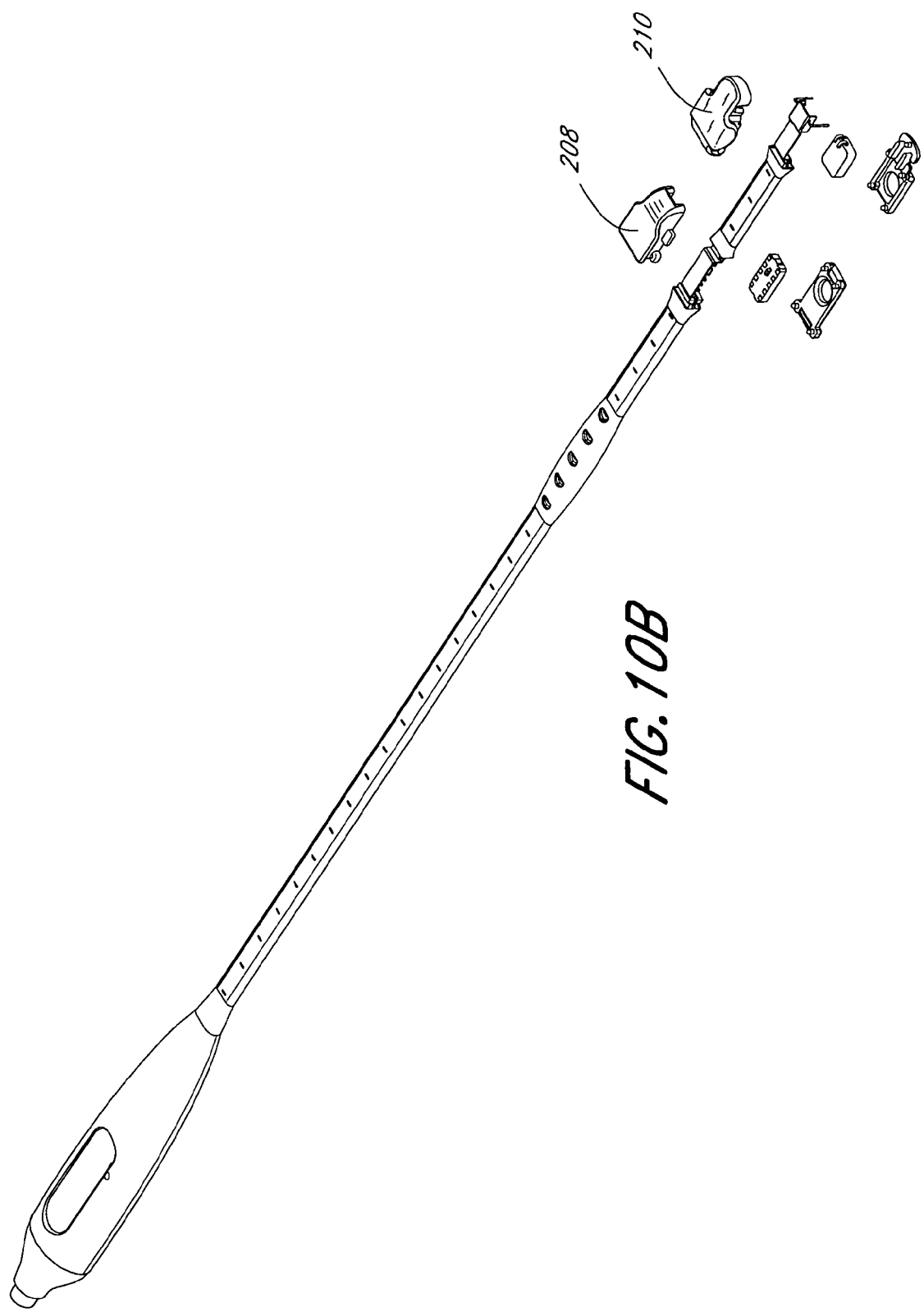
FIG. 10B illustrates an exploded view of the reusable component, according to an embodiment of the disclosure.

FIG. 10 illustrates an exploded view of an embodiment of disposable sensor component 206. As shown in FIG. 10, disposable sensor component 206 comprises a plurality of layers. For example, disposable sensor component 206 includes a base tape 1038. This base tape 1038 is preferably transparent polyethylene approximately 0.001 inches thick. Such material can be purchased from various sources, such as Product Number 3044 from Avery Dennison Medical of 7100 Lindsey Dr., Mentor, Ohio, 44060. As with all dimension recitations herein, an artisan will recognize from the disclosure herein that the dimensions of a particular layer may advantageously be redesigned according to various design desires or needs, and layers may be added or combined without departing from the scope of the present disclosure.

A second layer comprises a tape or web layer 1040. This layer is preferably white polypropylene also approximately 0.001 inches thick. One potential source for this material is Scapa North America, 540 North Oak Street, Inglewood, Calif., 90302, specifically product number P-341. Tape layer 1040 also has windows 1054 that allow light energy emanating from the sensor emitters to pass through this layer to the measurement site 426 and also allows the light to pass through to the detector. The windows 1054 may be holes, transparent material, optical filters, or the like. In the preferred embodiment, base tape 1038 does not have windows 1054. Base tape 1038 is preferably generally clear as discussed above. This allows light to pass through the tape from the sensor, while also generally reducing contamination of the sensor components. Disposable component 206 also includes clip 218 and assembly/disassembly clip 216. In an embodiment, information element 136 resides in a depression or slot within clip 218, preferably affixed in place by adhesives and/or mechanical structure. In an embodiment, a polyester film layer 1042 sandwiches the clips 216, 218 in place. In an embodiment the polyester film layer 1042 is generally clear and approximately 0.003 inches thick. Polyester film layer 1042 also includes slots 1044 to allow the vertical elements of assembly/disassembly clip 216 and front holding clip 218 to protrude therefrom and to allow polyester film layer 1042 to sit relatively flatly against the bases of assembly/disassembly clip 216 and front holding clip 218. Front stop 220 may be connected to the vertical elements of front holding clip 218 with polyester film layer 1042 therebetween.

The disposable portion 204 also includes light-blocking layer 1046, preferably made of metalized polypropylene approximately 0.002 inches thick. This is a commercially available product available, for example, as Bioflex™ RX48P. Light-blocking layer 1046 has cut-outs 1048 adapted to accept assembly/disassembly clip 216 and front holding clip 218. Light-blocking layer 1046 increases the likelihood of accurate readings by preventing the penetration to the measurement site of any ambient light energy (light blocking) and the acquisition of nonattenuated light from the emitters (light piping). Above light blocking layer 1046 is an opaque branding layer 1047 also having cut-outs 1048. This branding layer may advantageously comprise manufacturer's logos, instructions or other markings. Disposable sensor component 206 also comprises face tape 1050. This face tape 1050 is preferably a clear film approximately 0.003 inches thick and may be obtained commercially through companies such as 3M (product number 1527ENP), located in St. Paul, Minn., 55144. Face tape 1050 has cut-outs 1052 adapted to accept assembly/disassembly clip 216 and front holding clip 218.

Additional Advantages

Figure 11:
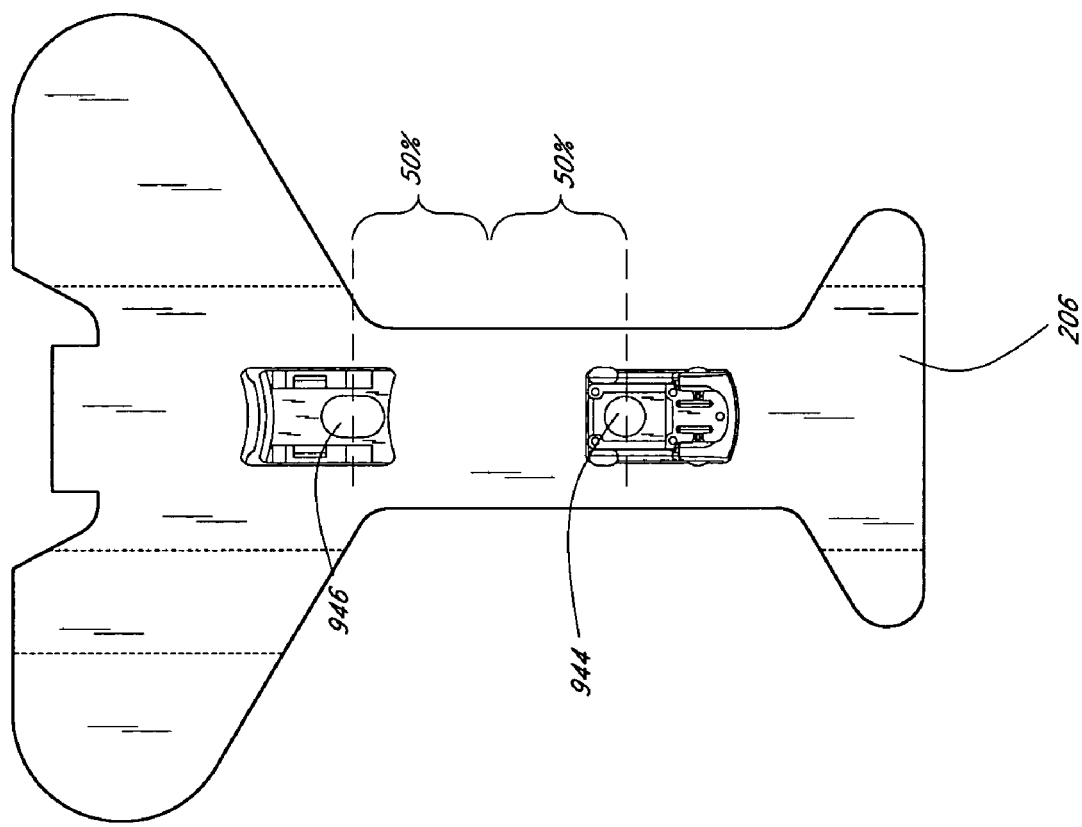
FIG. 11 illustrates top planar and side views of component placement of conventional sensors.
Figure 11:
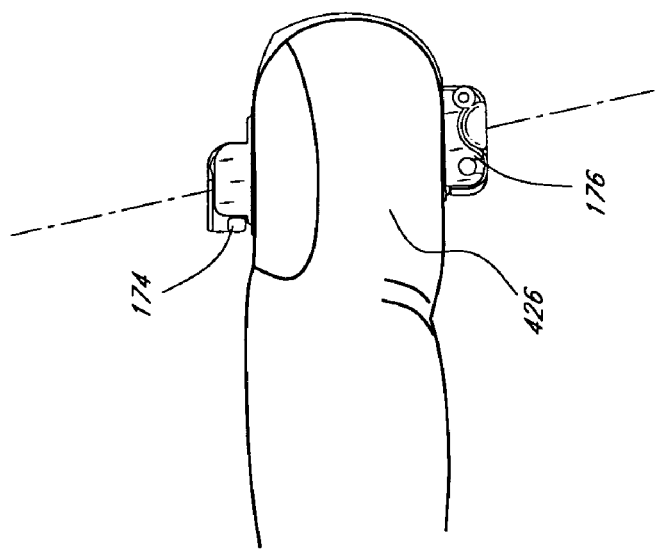

FIG. 11 illustrates a disposable sensor highlighting issues relating to sensor positioning. Generally, when applying the sensor of FIG. 11, a caregivers will split the center portion between the emitter and detector around, for example, a finger or toe. This may not be ideal, because as shown, it places the emitter 174 and detector 176 in a position where the optical alignment may be slightly or significantly off.

Figure 12:
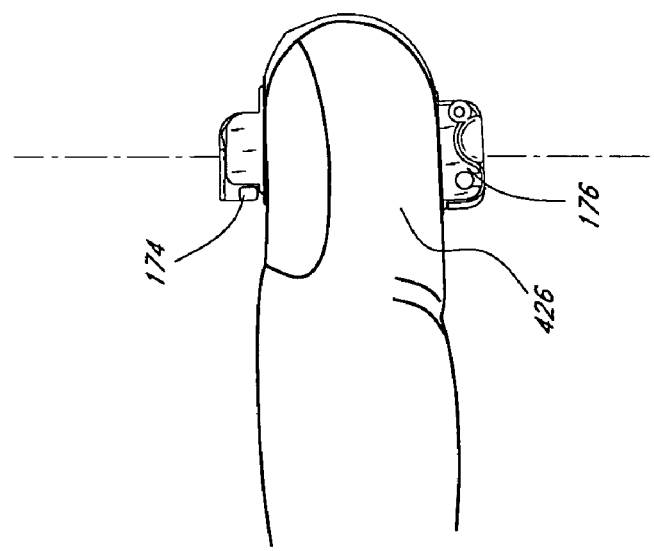
FIG. 12 illustrates top planar and side views of component placement according to an embodiment of the disclosure.
Figure 12:
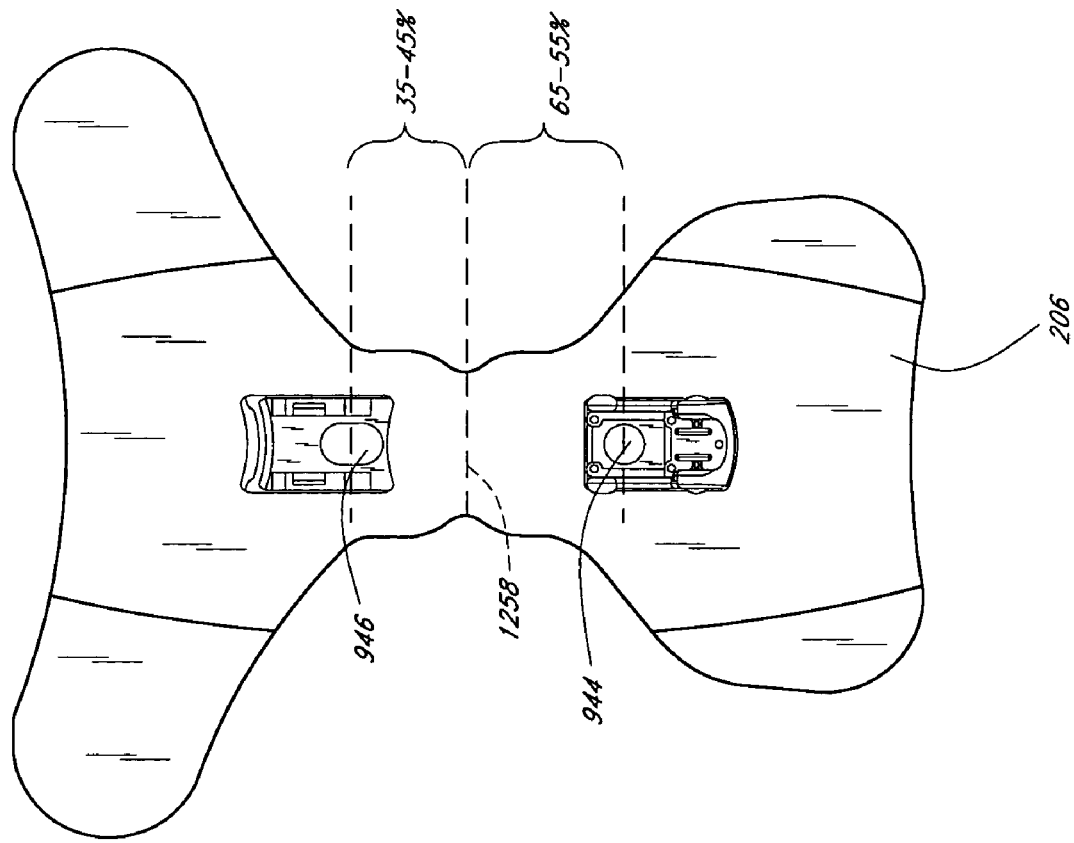

FIG. 12 illustrates an embodiment of the disposable component 206 including scoring line 1258. Scoring line 1258 is particularly advantageous, because it aids in quick and proper placement of the sensor on a measurement site 426. Scoring line 1258 lines up with the tip of a fingernail or toenail in at least some embodiments using those body parts as the measurement site. FIG. 12 also illustrates the disposable component 206 where the distance between the windows 944, 946 is purposefully off center. For example, in an embodiment, the clips 216 and 218 will position the sensor components off center by an approximate 40%-60% split. A scoring line 1258 preferably marks this split, having about 40% of the distance from window 946 to window 944 as the distance between window 946 and the scoring line 1258. This leaves the remaining approximately 60% of the distance between the two windows 944, 946 as the distance between scoring line 1258 and window 944.

Scoring line 1258 preferably lines up with the tip of the nail. The approximately 40% distance sits atop a measurement site 426, such as the figure shown in a generally flat configuration. The remaining approximately 60% of the distance, that from the scoring line 1258 to window 944, curves around the tip of the measurement site 426 and rests on the underside of the measurement site. This allows windows 944, 946—and thus in turn detector 176 and emitter 174—to optically align across measurement site 426. Scoring line 1258 aids in providing a quick and yet typically more precise guide in placing a sensor on a measurement site 426 than previously disclosed sensors. While disclosed with reference to a 40%-60% split, the off center positioning may advantageously comprise a range from an about 35%—about 65% split to an about 45%—about 55% split. In a more preferred embodiment, window 944 to scoring line 1258 would comprise a distance of between about 37.5% and about 42.5% of the total distance between window 944 and 946. In the most preferred embodiment, the distance between window 944 and scoring line 1258 would be approximately 40% of the total distance between window 944 and window 946, as is illustrated in FIG. 12. With a general 40%-60% split in this manner, the emitter and detector should generally align for optimal emission and detection of energy through the measurement site.

Figure 13:
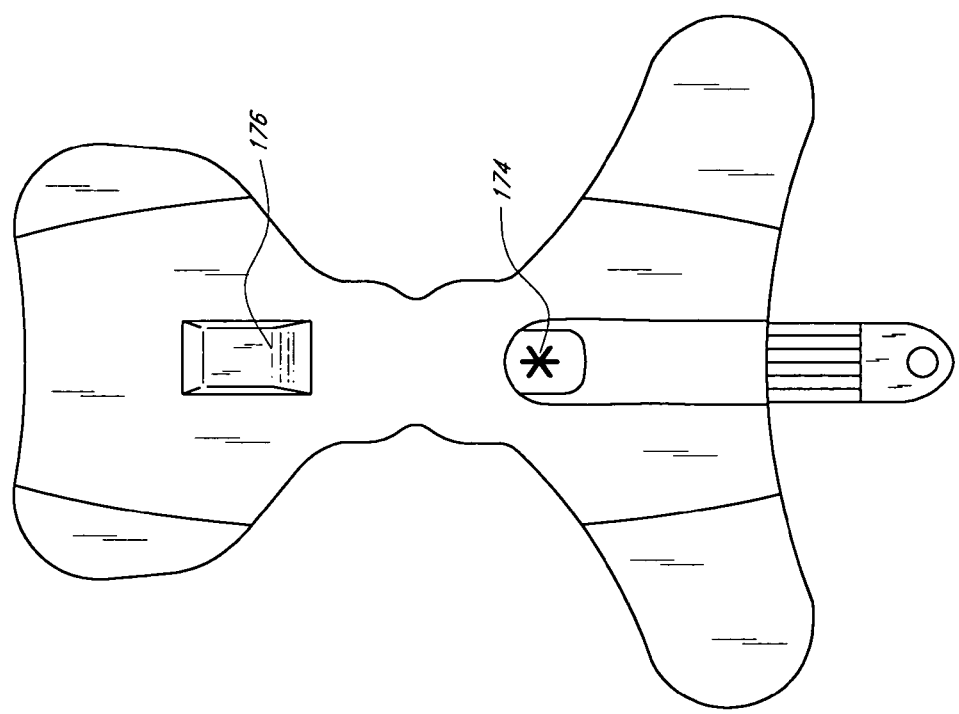
FIG. 13 illustrates a top down planar view of a disposable sensor, according to an embodiment of the disclosure.

FIG. 13 illustrates a disposable sensor containing many of the features discussed in this disclosure. Based on the disclosure herein, one of ordinary skill in the art may advantageously fix the components discussed herein to form a disposable sensor without moving beyond the scope of the present disclosure.

Although the sensor disclosed herein with reference to preferred embodiments, the disclosure is not intended to be limited thereby. Rather, a skilled artisan will recognize from the disclosure herein a wide number of alternatives for the sensor. For example, the emitter and detector locations may be in the opposite housings from what was discussed here. It is also possible that the assembly/disassembly clip and sensor clip would be reversed in relation to the casings into which they clip. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A noninvasive optical sensor having a reusable portion and a disposable portion and being capable of outputting a signal indicative of light attenuated by body tissue usable to determine one or more physiological characteristics of the body tissue, the optical sensor comprising:
    a reusable component including at least one energy emitter and a detector capable of detecting energy attenuated by body tissue and capable of outputting a signal usable to determine one or more physiological characteristics of the body tissue, the at least one energy emitter being housed in a first casing and the detector being housed in a second casing, wherein the first and second casings are connected by a flexible connector; and
    a disposable component including a first clip mechanically matable with the first casing and a second clip mechanically matable with the second casing, wherein at least one of the first and second clips mechanically mates in a substantially fixed manner with respect to the appropriate casing while the other of the first and second clips mechanically mates in a vertically and horizontally open manner with respect to the appropriate casing, wherein application of the disposable component to the body tissue moves the vertically and horizontally open mating to be at least substantially vertically fixed.

2. The optical sensor of claim 1, wherein removal of the disposable component from the body tissue moves the substantially vertically fixed mating back to being vertically and horizontally open, thereby permitting straightforward separation of the disposable and the removable components.

3. The optical sensor of claim 1, wherein the disposable component comprises an information element, and wherein assembly of the reusable and disposable components creates and electrical connection between the information element and conductors of the reusable element.

4. The optical sensor of claim 1, wherein the disposable component positions the first and second casings off center such that distance from a center to one of the first and second casings ranges from about 35% to about 45% of the distance.

5. The optical sensor of claim 1, wherein the disposable component positions the first and second casings off center such that distance from a center to one of the first and second casings ranges from about 65% to about 55% of the distance.

6. A reusable element of a noninvasive optical sensor, the reusable element comprising:
    at least one energy emitter;
    a detector capable of detecting energy attenuated by body tissue and capable of outputting a signal usable to determine one or more physiological characteristics of the body tissue;
    a first casing housing one of the at least one energy emitter and the detector, the first casing including a plurality of tabs capable of sliding vertically within a slot in an appropriate disposable attachment upon assembly with the disposable attachment and sliding horizontally along a groove in the disposable attachment during attachment thereof to the body tissue, thereby substantially vertically fixing the first casing with respect to the disposable attachment;
    a second casing housing the other of the at least one energy emitter and the detector, the second casing including an electrical contact capable of electrically communicating with electrical components in the disposable attachment and including a plurality of mechanical structures capable of substantially fixing the second casing with respect to the disposable attachment upon assembly; and
    a reinforced flexible connector connecting the first casing to the second casing.

7. A disposable element of a noninvasive optical sensor, the disposable element comprising:
    a first receptacle capable accepting a first housing of a first electronic element of reusable component of the noninvasive optical sensor, the first receptacle comprising vertical and horizontal slots for vertically receiving tabs of said first housing upon assembly and horizontally receiving the tabs upon application to body tissue;
    a second receptacle capable of accepting a second housing of a second electronic element of a reusable component, at least one of the first and second electronic elements comprising a detector capable of detecting light attenuated by body tissue, the second receptacle comprising an electrical contact and a front stop comprising a fluid resistance material, wherein the electrical contact is at least partially protected by the front stop from fluid contamination when the reusable component is assembled with the disposable element; and an information element electrically connected to the electrical contact.

8. The disposable element of claim 7, wherein the disposable element is scored.

9. A method of assembling a noninvasive optical sensor, the method comprising:
providing a reusable portion including housings for electronic elements;
providing a disposable portion including clips for receiving said housings, wherein a first housing is substantially vertically received and when received, substantially fixes said first housing with respect to said disposable portion, and wherein a second housing is substantially vertically received;
snapping said first housing into one of said clips on said disposable portion, thereby creating an electrical contact between conductors of said reusable portion and an information element of said disposable portion; and
sliding said second housing into another of said clips on said disposable portion, to form an assembled noninvasive optical sensor.

10. The method of claim 9, further comprising attaching the assembled sensor to a measurement site.

* * * * *